(12) United States Patent  
Surareungchai et al.

(10) Patent No.: US 8,945,370 B2  
(45) Date of Patent: Feb. 3, 2015

(54) ELECTROCHEMICAL DETECTION OF CAPSAICINOID COMPOUNDS IN A SAMPLE

(75) Inventors: Werasak Surareungchai, Bangkok (TH); Chatuporn Phanthong, Bangkok (TH)

(73) Assignee: Agricultural Research Development Agency, Bangkok (TH)

(*) Notice: Subject to any disclaimer, the term of this patent is extended or adjusted under 35 U.S.C. 154(b) by 0 days.

(21) Appl. No.: 14/008,212

(22) PCT Filed: Mar. 30, 2012

(86) PCT No.: PCT/TH2012/000014  
§ 371 (c)(1),  
(2), (4) Date: Sep. 27, 2013

(87) PCT Pub. No.: WO2012/134408  
PCT Pub. Date: Oct. 4, 2012

(65) Prior Publication Data  
US 2014/0014534 A1 Jan. 16, 2014

(30) Foreign Application Priority Data  
Mar. 31, 2011 (TH) .............................. 1101000475

(51) Int. Cl.  
*G01N 27/26* (2006.01)  
*G01N 27/48* (2006.01)  
*G01N 27/327* (2006.01)

(52) U.S. Cl.  
CPC ............ *G01N 27/48* (2013.01); *G01N 27/3277* (2013.01)  
USPC ...................................... 205/787; 205/780.5

(58) Field of Classification Search  
CPC .............................. G01N 33/02; G01N 33/18  
See application file for complete search history.

(56) References Cited

U.S. PATENT DOCUMENTS

2011/0014633 A1  1/2011  Ifuku et al.

FOREIGN PATENT DOCUMENTS

| EP | 2261648 A1 | 12/2010 | |
|---|---|---|---|
| JP | H1183800 A | 3/1999 | |
| JP | 2009150836 A | 7/2009 | |
| JP | 2009250746 A | 10/2009 | |
| WO | 2009116534 A1 | 9/2009 | |
| WO | WO 2009115840 A1 * | 9/2009 | ............. G01B 27/48 |

OTHER PUBLICATIONS

Kachoosangi, R. et al. "Carbon nanotube-based electrochemical sensors for quantifying the 'heat' of chili peppers: the adsorptive stripping voltammetric determination of capsaicin," Analyst, Jul. 2008, 133(7), pp. 888-895. Abstract attached.

* cited by examiner

*Primary Examiner* — Alex Noguerola  
(74) *Attorney, Agent, or Firm* — Nath, Goldberg & Meyer; Jerald L. Meyer

(57) ABSTRACT

An electrochemical method for capsaicinoid and/or related compound detection in a sample by way of a screen printed electrode having a working electrode, a reference electrode, and a counter electrode. The working electrode can be screen-printed using conductive carbon ink; the reference electrode can be screen printed using conductive carbon ink; and the counter electrode can be screen printed using silver/silver chloride. The method includes contacting the electrode with the sample in the presence of electrolyte solution, and determining whether a change in redox potential occurs by way of differential pulse voltammetry, wherein a modulation amplitude is between approximately 0.1 volt/min and approximately 2.0 volt/min, a step potential is between approximately 0.0005 volt and approximately 0.01 volt, a modulation time is 0.05 seconds, and a corresponding interval time is approximately 0.5 second.

7 Claims, 6 Drawing Sheets

ELECTROCHEMICAL DETECTION OF CAPSAICINOID COMPOUNDS IN A SAMPLE

TECHNICAL FIELD

The present disclosure relates generally to techniques for detecting capsaicinoids in a sample. More particularly, the present disclosure is directed to electrochemical technique for detecting capsaicinoids in a sample. Aspects of the present disclosure are further directed to electrode designs that can substantially reduce, avoid, or suppress the occurrence of electrode degradation.

BACKGROUND

The piquancy, pungency, "spicy heat," or "spicy hotness" of various substances depends upon particular chemical compounds carried by the substances. The sensation of piquancy, pungency, "spicy heat," or "spicy hotness" is a chemesthetic phenomenon involving somatosensory nerve pathways (e.g., nociceptive pathways), and is distinct from other types of taste phenomena. For purpose of simplicity and to aid understanding, piquancy, pungency, or "spicy hotness" is referred to hereafter as spiciness.

Commonly, the sensation of spiciness results from tissue exposure to compounds known as capsaicinoids. The capsaiciniods are amides formed from condensation of vanillylamine and fatty acids of different chain lengths. The particular forms of different natural capsaicinoids depend on the number of lateral chain carbon(R) and/or the presence, absence, or extent of (un)saturation. Capsaicinoids are synthesized naturally, for instance, in the placenta of chili fruits from enzymatic condensation of vanillamine and different-sized fatty acid chains, which are elongated by a fatty acid synthase. The capsaicinoind family includes capsaicin, dihydrocapsaicin, and other compounds shown below.

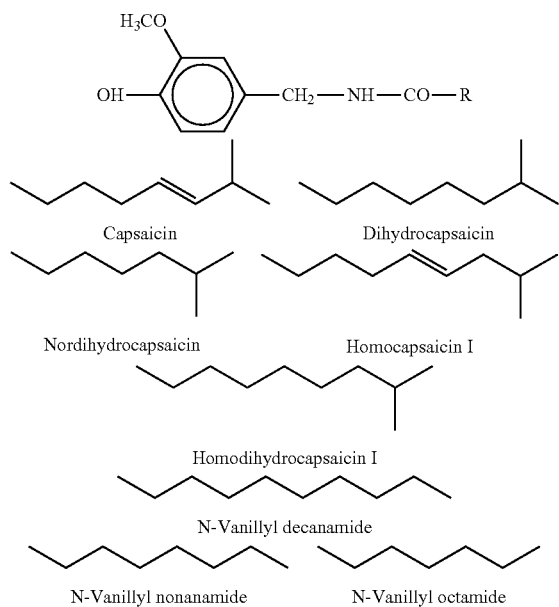

A conventional measurement of spiciness is the Schoville Heat Unit (SHU), which is measured by way of the Schoville organoleptic technique or test (See W.Scoville, *J Am Pharm. Assoc.*, 1, 453, (1912)). According to this technique, a pepper extract is diluted in sugar syrup until the heat or pungency is no longer detectable to the tongues of a panel of five tasters (specially trained volunteers). However, the greatest weakness of the Scoville Organoleptic Test is its imprecision, because it relies on human subjectivity. An alternative technique for quantitative measurement of spiciness is high pressure liquid chromatography (HPLC), which measures spiciness in terms of ASTA pungency units. While HPLC is more objective and accurate than the traditional Scoville Unit, it is also much more complex and costly.

Some researches have additionally studied electrochemical techniques for detecting capsaicinoids. Electrochemical techniques involve determining relationships between electrical potential and the concentration of redox species at an electrode surface. For detecting capsaicinoids, electrode surfaces have been modified by way of nano-scale structures such as Multi-walled Carbon nanotubes (MWCNTs). However, such electrode surface modification results in unnecessary expense and complexity, and can limit electrode performance or measurement reliability in certain situations. Therefore, there is a need for more cost efficient and/or simpler techniques for detecting spiciness in a sample.

SUMMARY

In accordance with an aspect of the present disclosure, a process for capsaicinoid and/or related compound detection in a sample includes contacting a screen printed electrode having a non-modified working electrode surface with the sample in the presence of an electrolyte solution; and determining whether a change in redox potential occurs by way of a voltammetry technique. A capsaiciniod can include or be, for instance, capsaicin and/or dihydrocapsaicin. An electrolyte can be selected from one or more of Brittion-Robinsson buffer, acetate buffer, phosphate buffer, potassium chloride buffer, methanol, and acetonitrile.

A screen-printed electrode in accordance with an embodiment of the present disclosure can include or be a screen-printed carbon electrode. In a particular embodiment, the screen printed electrode includes a screen-printed carbon working electrode and a screen printed silver/silver chloride reference electrode. The working electrode can provide a chemical reaction surface that is substantially non-modified, essentially non-modified, non-modified, substantially bare, essentially bare, or bare.

A voltammetry technique can be selected from one or more of cyclic voltammetry (CV), square wave voltammetry (SWV), linear scan voltammetry (LSV), differential pulse voltammetry (DPV), and normal pulse voltammetry (NPV). For instance, a voltammetry technique can include or be differential pulse voltammetry by way of a modulation amplitude between 0.1 to 2.0 volt/min, a step potential between approximately 0.0005 volt and approximately 0.01 volt, a modulation time of approximately 0.05 second, and a interval time of approximately 0.5 second.

DETAILED DESCRIPTION

Figure 1A:
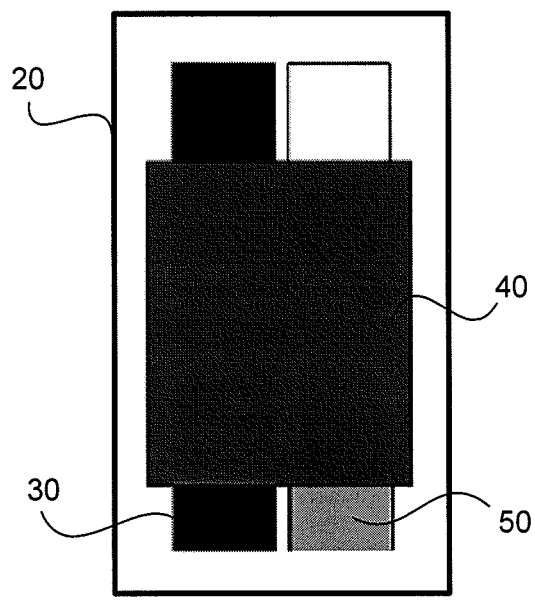
FIG. 1 is a schematic illustration of a representative screen printed bare Carbon electrode in accordance with an embodiment of the present disclosure.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. Additionally, unless explicitly stated otherwise, in the description herein, the recitation of particular numerical values or value ranges is taken to be a recitation of particular approximate numerical values or approximate value ranges.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a process, a constituent or ingredient, a physical parameter, or a value depending upon the type of set under consideration.

It will be understood that the details presented herein describe particular representative embodiments of the present disclosure, and are not intended to limit the scope of the present disclosure and/or associated claims. Unless define otherwise, all technical and scientific terms used herein have the same meaning as commonly understood by one of ordinary skill in the relevant art.

Embodiments in accordance with the present disclosure are directed to electrochemical techniques and corresponding electrodes or electrode structures for detecting, estimating, measuring, characterizing, and/or analyzing the piquancy, pungency, spicy heat, or spicy hotness (hereafter "spiciness") corresponding to chemical compounds in a sample, where such compounds include capsaicinoids, capsaicinoid analogues, and/or related types of compounds (e.g., gingerol or shogaol) that include an OH group in their chemical structure, for instance, an OH group carried by an aromatic ring such as a phenolic type functional group.

Electrodes in accordance with embodiments of the present disclosure exhibit a simple structure, which in various embodiments omits, avoids, or excludes unnecessary surface modification, particularly by way of omitting, avoiding, or excluding surface modification involving the use of nano-scale materials or structures (e.g., intentionally or specifically introduced/engineered nano-scale structures) such as Carbon nanotubes (CNTs), for instance, Multi-walled CNTs (MWCNTs). MWCNT are known to suffer intercalation, leading to potential exfoliation when used for electrode materials, which can result in electrode degradation/lack of electrode reliability. Furthermore, when using electrodes having MWCNT for detecting the spiciness of samples including capsaicinoids, capsaicin and dihydrocapsaicin can undesirably lead to MWCNT passivation, potentially interfering with the detection, estimation, or measurement of additional/other compounds in the sample associated with spiciness. In accordance with embodiments of the present disclosure, the avoidance of unnecessarily complex or costly surface modification, or the avoidance of surface modification entirely, results in readily manufacturable, inexpensive electrodes or electrode structures that can more successfully and/or more reliably detect, estimate, or measure the spiciness of capsaicinoids and/or related compounds compared to prior electrode structures involving MWCNTs.

The phenolic functional group of capsaiciniods can be oxidised by way of an electrochemical technique. In particular, such oxidation involves an o-alknoxyphenol group of a capsaicinoid at a working electrode, which is hydrolysed to form an o-benzoquinone group. The o-benzoquinone group subsequently facilitates or enables a reversible redox reaction at the working electrode to form an o-hydroxylphenol group.

In various embodiments in accordance with the present disclosure, a set of capsaicinoids can be selected from a group including or consisting of capsaicin, dehydrocapsaicin, nohydrocapsaicin, homocapsaicin I, dihomocapsaicin I, N-vanillyl decanamide, N-vanillyl nonanamide, and N-vanillyl octamide. In particular embodiments, a set of capsaicinoids includes or is capsaicin and dihydrocapsaicin.

For capsaicin and dihydrocapsaicin, an oxidation reaction can occur on an aromatic ring similar or corresponding to a phenolic functional group when it receives a proper electrical potential. Such processes are illustrated below:

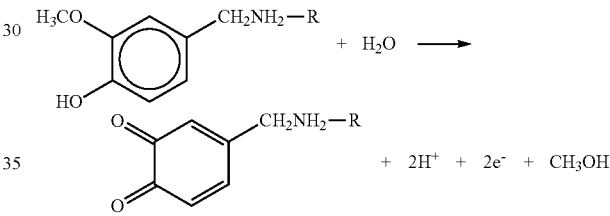

where R is $-CO(CH_2)_4CH=CHCH(CH_3)_2$ of capsaicin.

Various prior studies have examined only one compound, or an undesirably limited number of compounds, such as only one specific capsaicinoid form (e.g., capsaicin itself). Furthermore, several prior studies examined capsaicin in the form of a pure, substantially pure, or significantly purified substance, the purification or generation of which can be unnecessarily costly, time consuming, and/or complicated. In multiple embodiments, the present disclosure is directed to an electrochemical method for detecting capsaicinoids and/or capsaicinoid family compounds in a sample in the absence of a pure, substantially pure, or significantly purified sample form. Particular embodiments disclose a process for detecting, estimating, and/or measuring an amount of capsaicin and dihydrocapsaicin in the absence of a pure substance form (e.g., associated with a sample that includes or carries impurities and/or non-capsaicin ingredients or constituents, such as a curry sample).

Aspects of the present disclosure additionally involve investigation of redox reaction ability, as well electrical interference in an electrochemical detection process, for example, corresponding to an electrolyte reagent, a solvent used for making a sample soluble (e.g., alcohol group such as ethanol or methanol), and other chemical agent(s) carried by or within a sample.

REPRESENTATIVE ASPECTS OF ELECTROCHEMICAL DETECTION OF CAPSAICINOIDS

In general, electrochemical detection involves a working electrode, a reference electrode, and a counter electrode. The working electrode provides a surface for a reduction or an oxidation reaction, depending on the electrode at which an electrochemical reaction under consideration takes place. The active potential of the working electrode is measured against a standard reference electrode. The reference electrode enables accurate measurement of the potential of the working electrode. The counter electrode is complementary to the working electrode, and serves as an electrode across which a driving potential is applied to activate the electrochemical reaction to achieve an intended or required oxidation or reduction reaction.

Electrical current resulting from the electrochemical reaction is amplified and, when plotted as a function of time, appears on an output, display, or recording device as a curve exhibiting a peak. Current (e.g., faradaic current) measured at the working electrode surface results from not only the redox reaction of interest, but also form other or unwanted redox reactions coming from the mobile phase, faradic noise, and from one or more sources of noise associated with the working electrode material itself, the solvent delivery system, and potentiostat type. Non-faradaic noise can be minimized by careful mobile phase production and cleaning of the electrode.

Various embodiments in accordance with the present disclosure utilize working electrodes made using convenient, readily available, inexpensive, and stable carbon, carbon based, or carbon related sources or materials. Depending upon embodiment details, a working electrode in accordance with the present disclosure can include or be a glassy carbon, pyrolytic carbon, or porous graphite electrode. A working electrode can additionally include one or more metals such as platinum, gold, silver, nickel, mercury, gold-amalgam and a variety of alloys. In multiple embodiments in accordance with the present disclosure, the working electrode surface is substantially unmodified, non-modified, or bare.

The reference electrode can include or be a solid silver material or wire coated with silver chloride. Alternatively, the reference electrode can include or be another type of electrode, such as a mercury and/or murcurous chloride or saturated calomel electrode (SCE). The reference electrode can include or be an a-hydrogen, platinum, or palladium electrode. The counter electrode is configured to reduce the redox species oxidized at the working electrode. Normally, platinum is used for this layer due to its high catalytic property. A thin layer of platinum can be deposited on a carrier material or substrate such as Fluoride doped Tin Oxide (FTO) by thermal decomposition, sputtering, or electrochemical deposition.

In various embodiments, one or more portions of the electrode, such as the working electrode, are produced by way of a screen printing technique in which conductive materials are screen printed on a substrate, support member, or carrier, which in multiple embodiments can include a polymer or plastic substrate such as polyvinyl chloride (PVC), polyethylene teraphthalate polyester (PET or PETP), or other type of polymer-based substrate. More particularly, the working electrode can be produced by screen printing conductive carbon inks or analogous/similar inks or materials in an electrode pattern onto a polymer based substrate. The reference electrode can also be produced by screen printing conductive carbon or analogous/similar inks or materials in an electrode pattern onto a substrate, and rescreened with silver/silver chloride. Screen printing techniques suitable for producing electrodes or electrode structures in accordance with embodiments of the present disclosure will be understood by those of ordinary skill in the relevant art.

Figure 1B:
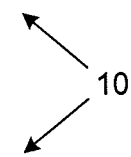

FIG. 1A is a schematic illustration of a representative electrode or electrode structure 10 configured for detecting, characterizing, estimating, or measuring spiciness in a sample in accordance with an embodiment of the disclosure. In an embodiment, the electrode 10 includes a substrate 20 that carries each of a working electrode 30, a reference electrode 40, and counter electrode 50. An electrode 10 in accordance with an embodiment of the present disclosure can exhibit a variety of geometries and/or dimensions, for instance, a planar or generally structure having an electrode surface extent or area between for instance, approximately 4 $cm^2$ and 25 $cm^2$, e.g., an electrode surface extent or area of approximately 1.3 cm×3.3 cm. FIG. 1B depicts a representative implementation of an electrode 10 in accordance with an embodiment of the present disclosure.

In various situations, samples containing a set of capsaicinoids and/or capsaicinoid family compounds can contain substances capable of contributing to or causing interference in a measurement or assay signal. Occasionally, interfering species in sample solution, such as an electrolyte and/or a solvent, can contribute to or provide direct interference current and/or mediated interference current. Such interfering species give rise to voltammograms showing the signal of the target substance improperly, hence leading to inaccurate or unreliable spiciness estimates or measurements. Embodiments in accordance with the present disclosure can reduce, substantially reduce, or eliminate the effect(s) of interfering substances or compounds by way of a suitable electrolyte, a suitable solvent, and/or proper sample solution preparation.

In multiple embodiments in accordance with the present disclosure, the electrochemical detection, estimation, measurement, characterization, or analysis of spiciness occurs in the presence of an electrolyte solution. Various types of electrolyte solutions can be used, including but not limited to Brittion-Robinsson buffer solution, acetate buffer solution, phosphate buffer solutions, potassium chloride buffer solution, and methanol or acetonitrile containing various supporting electrolytes. In particular embodiments, an electrolyte solution includes or is potassium chloride buffer solution owing to its efficiency and low cost.

In certain embodiments, a solvent used for preparing a sample solution can be selected from a set of alcohols, such as at least one $C_{1-3}$ alcohol having low or relatively low molecular weight, and/or at least one $C_{4-20}$ alcohol having higher or relatively high molecular weight, wherein a $C_{1-3}$ alcohol can be selected from methanol, ethanol, and propanol; and a C4-20 alcohol can be selected from butanol, pentanol, hexanol, octanol, decanol, octadycylalcohol, benzylalcohol, penylethyalcohol, isopropylbenthyalcohol, and cumylalcohol. In multiple embodiments, a solvent includes ethanol. Depending upon embodiment details, a molar ratio of alcohol to sample can range from approximately 30 to one approximately 1000.

Multiple electrochemical techniques are suitable for use with embodiments of the present disclosure, such as potentionmetry, coulommetry, and voltammetry. One electrochemical technique that can be used in certain embodiments of the present disclosure is amperometry. According to this technique, current is measured during a read pulse in which a constant potential is applied across a working electrode and counter electrode of a sensor strip while measurement quantifies a rate at which the electrochemically active species, the analyte, is being oxidised or reduced proximate to a working electrode. In various embodiments, a voltammetry technique is utilized, which can include or be cyclic voltammetry (CV), square wave voltammetry (SWV), linear scan voltammetry (LSV), differential pulse voltammetry (DPV), and normal pulse voltammetry (NPV). In several embodiments, a voltammetry technique includes or is differential pulse voltammetry. Differential pulse voltammetry can enhance detection, estimation, characterization, measurement, and/or analysis accuracy and precision, along with reducing detection, estimation, characterization, measurement, or analysis completion time. In multiple embodiments, differential pulse voltammetry involves a pulse modulation amplitude between approximately 0.02 and 2.00 volt/min, for example, approximately 0.1 to 2.0 volt/min (e.g., about 0.15 volt/min). Additionally, a step potential is approximately 0.0005 volt to 0.01 volt; and a modulation time is approximately 0.05 second and a corresponding modulation interval is approximately 0.5 second.

Figure 2:
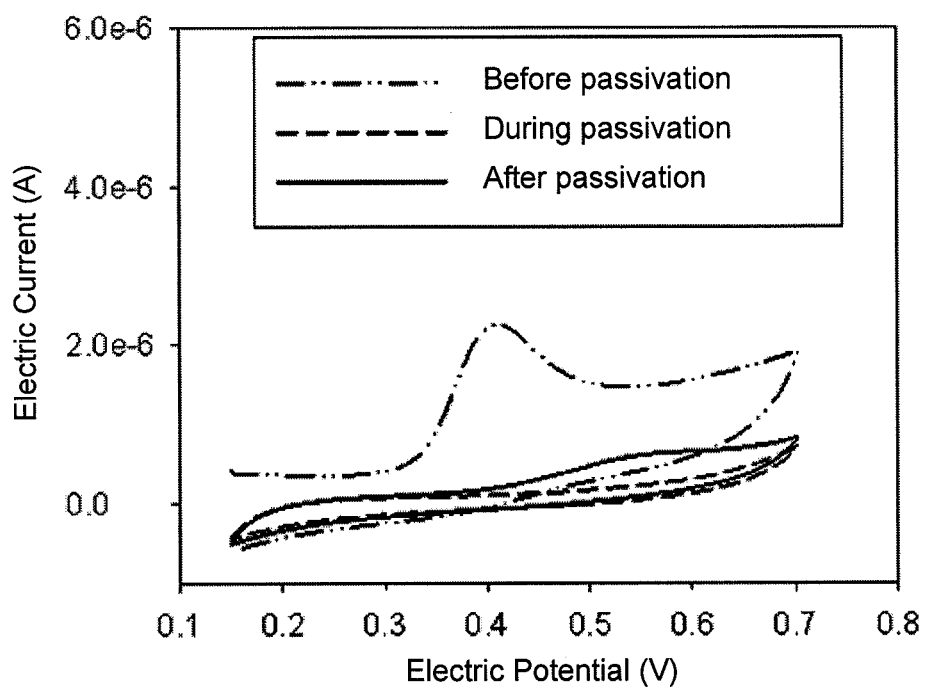
FIG. 2 illustrates non-steady state electrochemical detection of capsaicin and corresponding passivation-related effects.

A disadvantage associated with some electrochemical techniques is that after applying a potential, a non-steady-state current will occur, which can give rise to passivation and/or fouling. A rate of current change with respect to time can be fast or very fast initially, but becomes slower over time due to the changing nature of an underlying diffusion process. A steady-state current cannot be obtained until the consumption rate of a reducing mediator at the electrode surface equals to the diffusion rate. Consequently, a measurement corresponding to non-steady-state current can be associated with more inaccuracy than a steady-state measurement. Capsaicinoids such as capsaicin and dihydrocapsaicin can provide a non-steady-state current so as to impede accurate detection, estimation, measurement, characterization, or analysis of analytes in a sample. It can be found that non-electrolyte agents capsaicin and dihydrocapsaicin are unable to interchange molecules at an electrode surface, which adversely affects or prevents establishment of a redox reaction. FIG. 2 shows detection of 0.65 mmol capsaicin and dihydrocapsaicin by way of cyclic voltammetry involving application of a potential (voltage) ranging between approximately 0.15 volt and approximately 0.7 volt. It was found that an oxidation peak decreases significantly, which can indicate passivation effects.

PARTICULAR NON-LIMITING
REPRESENTATIVE EXAMPLES

Starting Materials/Reagents
  1. Sodium dihydrogen phosphate (Merck, Germany)
  2. Disodium hydrogen phosphate (Merck, Germany)
  3. Acetic acid (Merck, Germany)
  4. Potassium chloride (Merck, Germany)
  5. Methanol (Merck, Germany)
  6. Acetonitrile (Sigma-Aldrich, USA)
  7. Capsaicin (Sigma-Aldrich, USA)
  8. Dihydrocapsaicin (Sigma-Aldrich, USA)
  9. Ethanol (BDH, England)
Electrodes
  10. Screen-Printed Electrode
  11. Glassy Carbon electrode
  12. Platinum electrode
  13. Silver/Silver Chloride electrode
Equipment and Instruments
  14. Electrochemical Instruments EcoChemie model PGSTAT 10 (Autolab, Netherland)
  15. Semiautomatic screen printer model DEK-S 248 (England)
  16. Centrifuge model spectrafuge 16M (USA)
  17. Sonicator Model 175 DAE (Crest Ultrasonic, Malesia)
  18. Hood Model Memmert UNB100-500 (Germany)
  19. Scale 4 digit Model Ohaus PA 214
  20. HPLC column
  21. HPLC controller Model SCL-10A
  22. UV detector Model SPD-10A (SHIMADZU Japan)
  23. PH meter Model UB-10 (Denver, USA)
Preparation of a Screen-Printed Electrode A screen-printed carbon electrode or electrode structure such as that shown in FIG. 1A and/or 1B having a working electrode and a reference electrode was prepared by screening conductive carbon ink onto polyvinyl chloride (PVC), for instance, by way of an automatic or semiautomatic screen printer. For the reference electrode, a rescreening process involved rescreening with a silver/silver chloride layer, and then baking the screen-printed carbon electrode at a temperature of approximately 55 Celsius for 24 hours. Working and reference electrodes were rescreened with insulator ink on an outermost, upper, or top surface of the electrode structure.

Sample Preparation

Electrolyte solution was prepared by dissolving potassium chloride with phosphate buffer in a molar range between approximately 0.1-0.2 molar. Particularly, an electrolyte solution for chili samples was prepared by dissolving approximately 0.2 molar potassium chloride with approximately 0.1 molar phosphate buffer, and an electrolyte for a food sample was prepared by dissolving approximately 0.1 molar potassium chloride with approximately 0.1 molar phosphate buffer.

Fresh Chili Sample Preparation

Preparation of a fresh chili sample occurred at ambient temperature. A mixture of approximately 2 g of fresh chili and approximately 1 ml of pure ethanol were ultrasonically vibrated for approximately 15 minutes. The mixture was centrifuged at a speed of approximately 35000 rpm for approximately 5 minutes, and spun down for a few minutes.

Dried Chili Sample Preparation

Preparation of a dry chili sample was performed at ambient temperature. A mixture of approximately 1 g of dried chili and approximately 1 ml pure ethanol were ultrasonically vibrated for approximately 15 minutes. The mixture was centrifuged at a speed of approximately 35000 rpm for approximately 5 minutes, and spun down for a few minutes. The sample was further diluted with electrolyte solution by a factor of approximately 500-1000.

Curry and Chili Paste or Powder/Dried Spicy Mixing Food Sample Preparation

Preparation of a dry spicy food sample was performed at ambient temperature. A mixture of approximately 1 g of dried spicy food and approximately 1 ml of pure ethanol were ultrasonically vibrated for approximately 15 minutes. The mixture was centrifuged at a speed of approximately 35000 rpm for approximately 5 minutes and spun down for few minutes. The sample was further diluted with electrolyte solution by a factor of approximately 30.

Chili and Pepper Sauce/Wet Spicy Food Sample Preparation

Preparation of a wet spicy food sample was performed at ambient temperature. A mixture of approximately 2 g of wet spicy food and approximately 1 ml of pure of ethanol were ultrasonically vibrated by ultrasonic for approximately 15 minutes. The mixture was centrifuged at a speed of approximately 35000 rpm for approximately 5 minutes, and spun down for few minutes. The sample was further diluted with electrolyte solution to by a factor of approximately 60.

Representative Detection Parameters Using Differential Pulse Voltammetry

Detection, estimation, measurement, characterization, and/or analysis of capsaicin and dihydrocapsaicins by way of differential pulse voltammetry involved parameters including modulation amplitude, step potential, and time in which modulation amplitude and step potential affect detection efficiency and/or sensitivity. Modulation amplitude affects the symmetry of a peak, whereas step potential affects peak height.

Appropriate parameters were selected and/or parameter refinement/optimization performed by scanning a sample containing a known concentration of capsaicin, for instance, approximately 0.15 mmol capsaicin. Optimizing modulation amplitude occurred by fixing modulation time to approximately 0.05 second, interval time to approximately 0.5 second, and step potential to approximately 0.0025 volt. Then, modulation amplitude was varied from approximately 0.02 to approximately 2.0 volt. The parameters are given in Table 1.

TABLE 1

| | | Determining appropriate modulation amplitude | | | | |
|---|---|---|---|---|---|---|
| Condition No. | modulation time (second) | interval time (second) | Step potential (volt/second) | Modulation amplitude (second) | Potential (Volt) | Current (microampere) |
| 1 | 0.05 | 0.5 | 0.00255 | 0.02 | 0.80 | 0.94 |
| 2 | 0.05 | 0.5 | 0.00255 | 0.04 | 0.80 | 0.71 |
| 3 | 0.05 | 0.5 | 0.00255 | 0.05 | 0.77 | 2.67 |
| 4 | 0.05 | 0.5 | 0.00255 | 0.07 | 0.76 | 4.15 |
| 5 | 0.05 | 0.5 | 0.00255 | 0.08 | 0.75 | 4.85 |
| 6 | 0.05 | 0.5 | 0.00255 | 0.09 | 0.75 | 5.54 |
| 7 | 0.05 | 0.5 | 0.00255 | 0.10 | 0.75 | 6.20 |
| 8 | 0.05 | 0.5 | 0.00255 | 0.15 | 0.71 | 8.08 |
| 9 | 0.05 | 0.5 | 0.00255 | 2.0 | 0.74 | 8.89 |

Table 1 illustrates the differential pulse voltammograms of 0.15 mmol capsaicin in range of approximately 0.02 to approximately 0.2 volt. The oxidation peak current of capsaicin varied more widely when increasing modulation amplitude. Similarly, the oxidation current also increased significantly when increasing the number of modulation amplitudes. Modulation amplitude at approximately 0.1 volt to approximately 2 volt provided the highest oxidation peak current.

Figure 3:
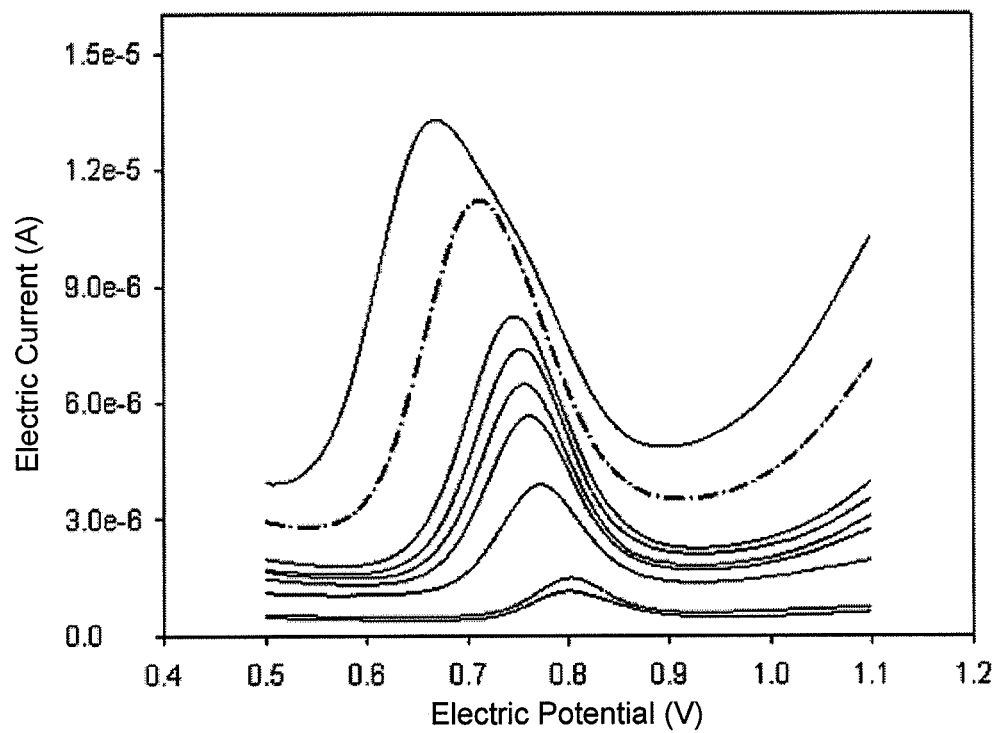
FIG. 3 is a voltammogram corresponding to 0.15 mmol capsaicin detection by way of differential pulse voltammetry at modulation amplitudes ranging from 0.02 volt to 2.0 volt.
Figure 4:
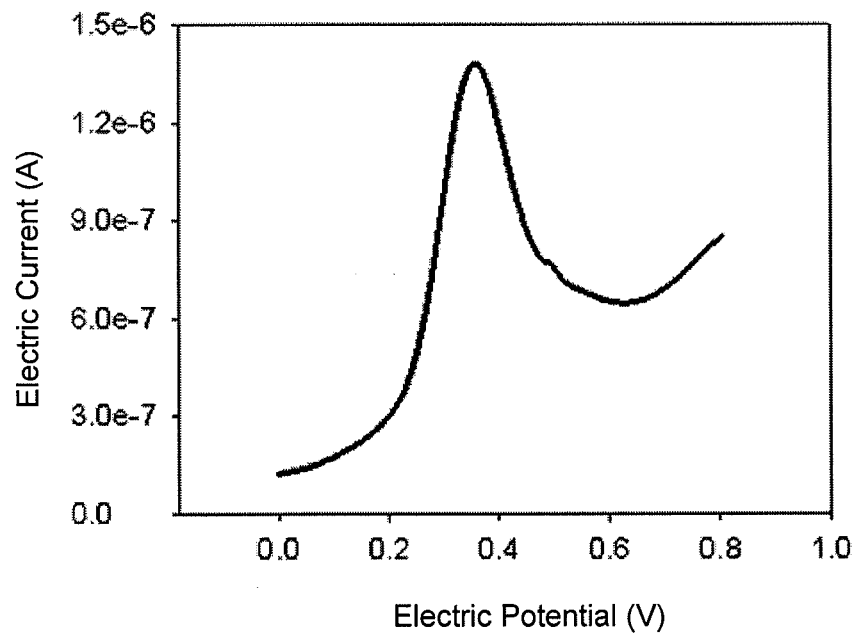
FIG. 4 is a voltammogram corresponding to Dried Khee noo chili.
Figure 5:
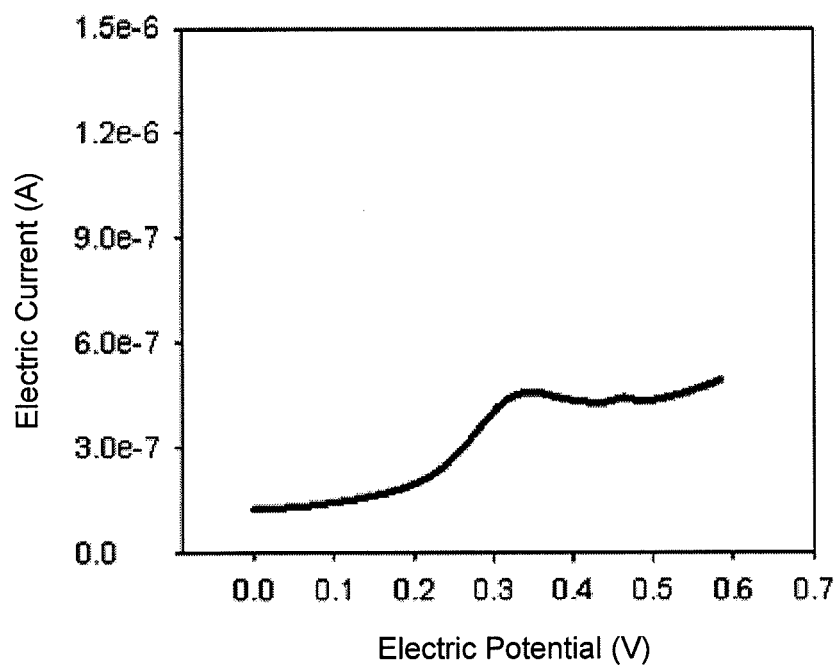
FIG. 5 is a voltammogram corresponding to Dried bell chili.
Figure 6:
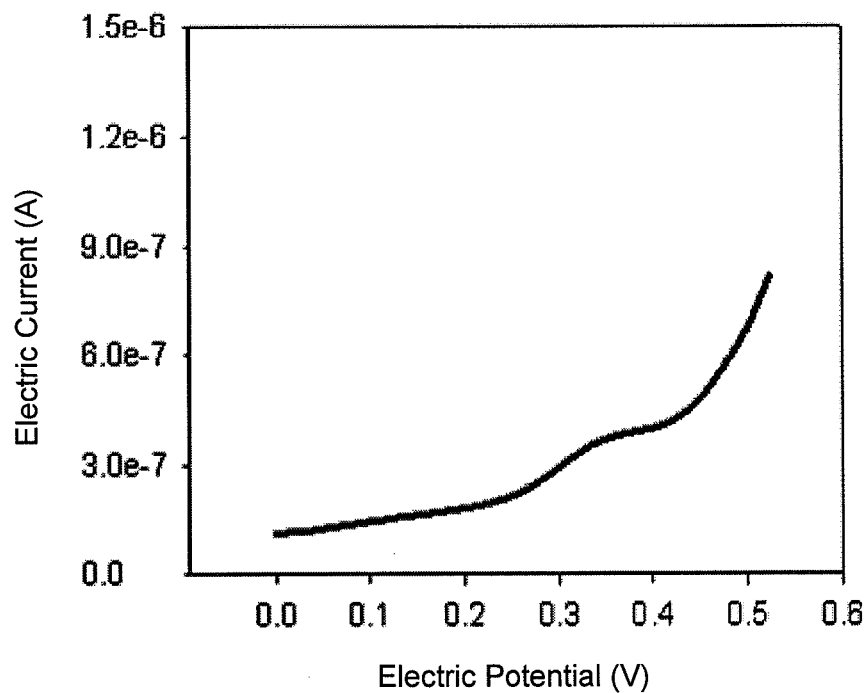
FIG. 6 is a voltammogram corresponding to Khee noo suan chili.
Figure 7:
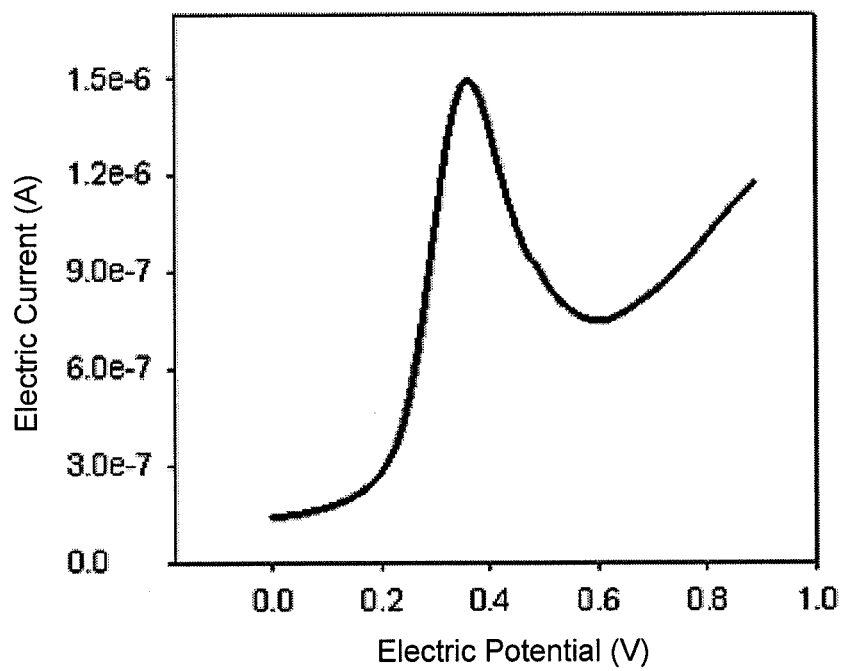
FIG. 7 is a voltammogram corresponding to Khee noo jinda chili.

FIG. 3 illustrates a voltammogram of 0.15 mmol capsaicin detected by differential pulse voltammetry at a modulation amplitude between approximately 0.02 volt to approximately 2.0 volt, which provides a highest oxidation peak current, but the shape of voltammogram is less symmetric than for that corresponding to approximately 0.15 volt. Consequently, a modulation amplitude of approximately 0.15 volt of is appropriate.

Optimization of step potential occurred by fixing modulation time at approximately 0.05 second, interval time at approximately 0.5 second, and step amplitude at approximately 0.15 volt. Then, rising step potential from approximately 0.0005 to approximately 0.01 volt. The results showed that a step potential at 0.01 volt is suitable for providing a highest oxidation current as shown in Table 2.

Appropriate differential pulse voltammetry parameters included a step potential of approximately 0.01 Volt/second, a modulation amplitude of approximately 0.15 Volt, a modulation time of approximately 0.05 second, and a interval time of approximately 0.5 second.

Example 1

Analysis of Capsaicin in Particular Chili Species by DPV

Electrolyte solution was prepared by dissolving potassium chloride with 0.1 molar phosphate buffer at pH 7. Particularly, electrolyte solution for chili sample was prepared by dissolving 0.2 molar potassium chloride with 0.1 molar phosphate buffer solution. Preparation of fresh chili sample was performed in ambient temperature. A mixture of approximately 2 g of fresh chili and ethanol 1 ml were ultrasonically vibrated for about 15 minutes. The mixture was centrifuged at a speed of approximately 35,000 rpm for 5 minutes, and spun down for few minutes. The sample was also diluted with electrolyte agent 500 times.

Spiciness detection or measurement was carried out by contacting the sample solution with the screen printed elec-

TABLE 2

| | | Determining appropriate step potential | | | | |
|---|---|---|---|---|---|---|
| Condition No. | modulation time (second) | interval time (second) | Step potential (volt/second) | Modulation amplitude (second) | Potential oxidation (Volt) | Oxidation Current (microampere) |
| 1 | 0.05 | 0.5 | 0.0005 | 0.15 | 0.19 | 1.32 |
| 2 | 0.05 | 0.5 | 0.0005 | 0.15 | 0.22 | 2.47 |
| 3 | 0.05 | 0.5 | 0.0005 | 0.15 | 0.22 | 2.67 |
| 4 | 0.05 | 0.5 | 0.0005 | 0.15 | 0.22 | 5.27 |
| 5 | 0.05 | 0.5 | 0.0005 | 0.15 | 0.22 | 4.48 |
| 6 | 0.05 | 0.5 | 0.0005 | 0.15 | 0.22 | 3.89 |
| 7 | 0.05 | 0.5 | 0.0005 | 0.15 | 0.24 | 6.02 |
| 8 | 0.05 | 0.5 | 0.0005 | 0.15 | 0.24 | 5.44 |
| 9 | 0.05 | 0.5 | 0.0005 | 0.15 | 0.24 | 9.17 | trode (e.g., by dropping the sample onto screen-printed electrode), and applying 0.0 volt to 1.0 volt of potential by differential pulse voltammetry using parameters including approximately 0.05 seconds of modulation time, approximately 0.5 second of interval time, approximately 0.01 volt/second of step potential, and approximately 0.15 volt of modulation amplitude. The concentration of capsaicin determined using DPV is given in Table 3, and the voltammograms correspondingly shown in FIGS. 4, 5, 6, and 7.

TABLE 3

Concentration of capsaicin in 4 different species of chili

| No. | Chili species | Potential oxidation (Volt) | Current oxidation (Ampere) | Scoville Unit |
|---|---|---|---|---|
| 1 | Bird Chili (light green) | 0.34 | 3.90E−7 | 608.65 |
| 2 | Bird Chili (green) | 0.33 | 1.54E−7 | 240.09 |
| 3 | Khee noo jinda chili | 0.35 | 9.85E−7 | 1,537.46 |
| 4 | Khee noo suan chili | 0.35 | 1.06E−6 | 1,651.58 |

Example 2

Analysis of Capsaicin in Dry and Wet Food Samples Using DPV

Electrolyte solution was prepared by dissolving potassium chloride with phosphate buffer 0.1 molar, pH 7. Particularly, electrolyte solution for chili sample was prepared by dissolving approximately 0.2 molar potassium chloride with approximately 0.1 molar phosphate buffers.

Preparation of a dry spicy food sample was performed at ambient temperature. Preparation involved dissolving a mixture of approximately 1 g of dry spicy food and ethanol 1 ml, then ultrasonically vibrating sample solution for approximately 15 minutes. The mixture was centrifuged at a speed of approximately 35,000 rpm for about 5 minutes, and spun down for few minutes. The sample was also diluted with electrolyte agent approximately 30 times.

Preparation of a wet spicy food sample was performed at ambient temperature. A mixture of approximately 2 g of fresh chili and approximately 1 ml ethanol were ultrasonically vibrated for approximately 15 minutes. The mixture was centrifuged at a speed of approximately 35,000 rpm for about 5 minutes, spun down for few minutes. The sample was also diluted with electrolyte agent approximately 60 times.

The detection was carried out by contacting sample solution with a screen printed electrode (e.g., by dropping sample solution onto the screen printed electrode), and then applying approximately 0.0 volt to approximately 1.0 volt by differential pulse voltammetry involving parameters including approximately 0.05 second of modulation time, approximately 0.5 second of interval time, approximately 0.01 volt/second of step potential, and approximately 0.15 volt of modulation amplitude. The concentration of capsaicin determined using DPV is given in Table 4.

TABLE 4

Capsaicin detection in samples using differential pulse voltammetry

| No. | Sample/Chili species | Name/Brand | Potential (Volt) | Current (Ampere) | Scoville Unit |
|---|---|---|---|---|---|
| Curry and chili paste/powder | | | | | |
| 1 | Green curry | Mae Sri | 0.34 | 1.07E−7 | 166.72 |
| 2 | Green Curry | Mae Ploy | 0.33 | 3.50E−7 | 545.74 |
| 3 | Green Curry | Nhamjai | 0.34 | 2.79E−7 | 436.15 |
| 4 | Green Curry | Lobo | 0.34 | 7.93E−7 | 1,237.12 |
| 5 | Green Curry | Mae Prono, | 0.34 | 6.48E−7 | 1,012.18 |
| 6 | Green Curry | Mae Kate | 0.34 | 3.57E−7 | 557.60 |
| 7 | Green Curry | Kindee | 0.24 | 3.42E−7 | 533.41 |
| 8 | Red Curry | Mae ploy | 0.34 | 4.74E−7 | 739.93 |
| 9 | Red Curry | Nhamjai | 0.34 | 2.17E−7 | 338.74 |
| 10 | Red Curry | BanWai | 0.36 | 6.15E−7 | 960.04 |
| Dry spicy food | | | | | |
| 11 | Panang Red Curry | Mae Sri | 0.33 | 3.00E−7 | 467.69 |
| 12 | Spicy Soup Powder | Kin Dee | 0.29 | 5.20E−7 | 123 |
| 13 | Spicy Soup Powder | Lobo | 0.30 | 5.64E−7 | 133 |
| 14 | Spicy Sauce with ginger | Mae Pranom | 0.34 | 2.89E−7 | 68 |
| 15 | Spicy Sauce | Lobo | 0.25 | 2.94E−8 | 7 |
| Wet spicy food including chili and pepper sauce | | | | | |
| 16 | Spicy Sauce with ginger | Mae Pranom | 0.34 | 2.89E−7 | 68 |
| 17 | Spicy Sauce | Lobo | 0.25 | 2.94E−8 | 7 |
| 18 | Chili Sauce | Sam Pukao | 0.28 | 2.24E−7 | 53 |
| 19 | Chili Sauce | Sriracha | 0.27 | 1.97E−7 | 47 |
| 20 | Chili Sauce (medium hot) | Goldenchef | 0.28 | 1.41E−7 | 33 |
| 21 | Chili Sauce (reduced sugar and salt) | Goodlife | 0.28 | 3.00E−8 | 7 |
| 22 | Chili Sauce (light hot) | PookaThong | 0.30 | 3.04E−7 | 72 |
| 23 | Chili Sauce (Extra hot) | Sukhum | 0.28 | 1.42E−7 | 34 |

TABLE 4-continued

Capsaicin detection in samples using differential pulse voltammetry

| No. | Sample/ Chili species | Name/ Brand | Potential (Volt) | Current (Ampere) | Scoville Unit |
|---|---|---|---|---|---|
| 24 | Pepper Sauce | Tabasco | 0.33 | 2.56E−7 | 61 |
| 25 | Red pepper and salt | Tabasco | 0.30 | 3.54E−7 | 84 |
| 26 | Habanera Sauce | Tabasco | 0.29 | 1.54E−6 | 364 |
| 27 | Chili Sauce (hot) | Wolf | 0.31 | 2.44E−7 | 58 |

Example 3

Analysis of Capsaicin by HPLC

In example three, sample solutions were prepared or produced in a manner analogous to that described above for Examples one and two.

The analysis of capsaicin by HPLC technique was performed by a reverse phase system. The sample was filtered through a 0.2 micron membrane, and then the filtered sample was injected through column C 18 with a sample injection volume of 100 μl. A mixture of 1% of acetic acid and acetonitrile in relation 50: 50 provided a mobile phase. The solvent flow rate was approximately 1.4 ml/minute and a column oven temperature was approximately 40°. The concentration of capsaicin determined using HPLC is given in FIGS. 8 and 9.

RESULTS AND DISCUSSION

Figure 8:
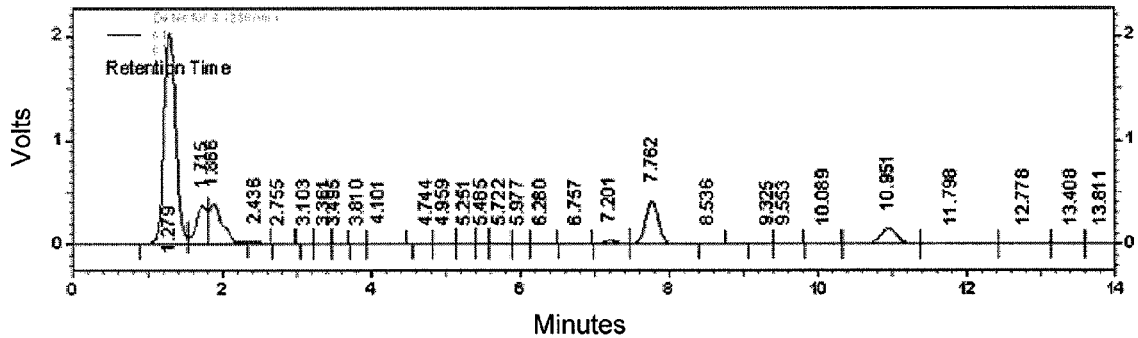
FIG. 8 is an HPLC analysis of capsaicin.
Figure 9:
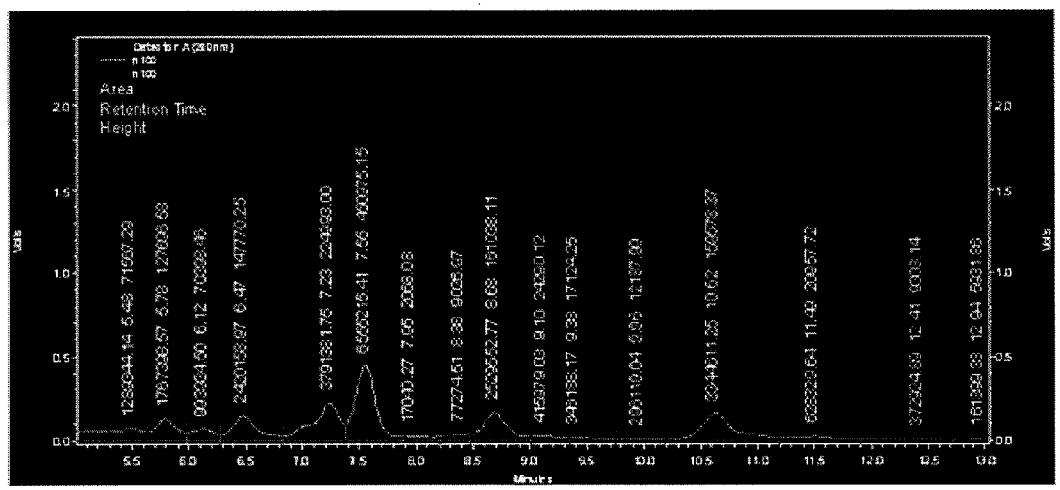
FIG. 9 is an HPLC analysis of capsaicin and dihydrocapsaicin in a green curry sample.

As shown in Examples one and two, the results of detecting capsaicin and dihydrocapsaicin by differential pulse voltammetry demonstrate an oxidation potential of approximately 0.3 to 0.4 volts, providing readily apparent oxidation peaks in the absence of current interference or in the presence of minimal or negligible current interference. The results suggest that the oxidation potential of each sample can slightly shift, for instance, depending on sample conductivity. In sample three, the results of HPLC analysis illustrated in FIG. 8 showed the oxidation peak of capsaicin and dihydrocapsaicin is found clearly at a retention time of approximately 7.8 and 10 seconds, whereas the retention time of capsaicin and dihydrocapsaicin in the sample had overlapping aspects as shown in FIG. 9. Furthermore, it was found the columns will be blocked when continuing to analyze 100 samples or more. Accordingly, results suggest that an electrochemical technique in accordance with the present disclosure can detect, estimate, measure, characterize, or analyze capsaicinoid quantity or concentration in a sample without the process of filtering and/or providing or making a pure substance.

Figure 10:
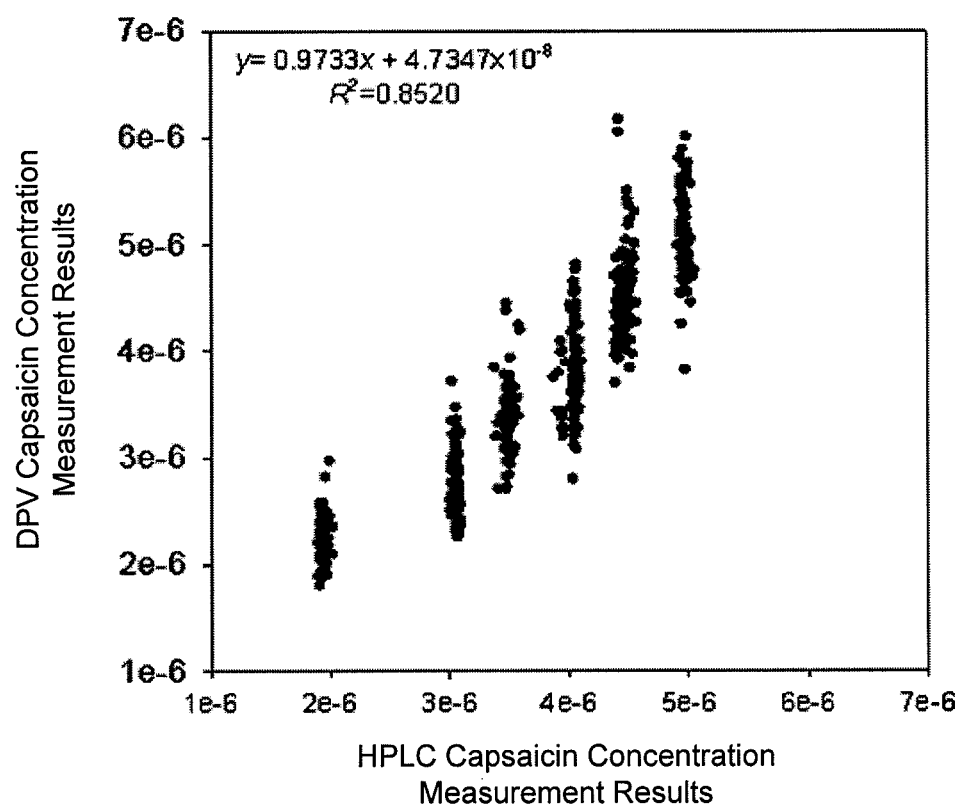
FIG. 10 is a correlation comparison of capsaicin detected by an HPLC technique and differential pulse voltammetry in accordance with an embodiment of the present disclosure.

Electrochemical detection of capsaicin and/or related compounds in accordance with embodiments of the present disclosure gives rise to detection or measurement results that are well correlated with results obtained by way of HPLC (which are themselves well correlated with measurements or estimates made by way of appropriately performed Scoville organoleptic tests). For instance, electrochemical detection of capsaicin and/or related compounds in accordance with embodiments of the present disclosure can provide detection or measurement accuracy and/or efficiency that is at least substantially identical to that for HPLC, as shown in FIG. 10.

Particular embodiments of the disclosure are described above for addressing at least one of the previously indicated problems. While features, functions, processes, process portions, advantages, and alternatives associated with certain embodiments have been described within the context of those embodiments, other embodiments may also exhibit such advantages, and not all embodiments need necessarily exhibit such advantages to fall within the scope of the disclosure. It will be appreciated that several of the above-disclosed features, functions, processes, process portions, advantages, and alternatives thereof, may be desirably combined into other different methods, processes, systems, or applications. The above-disclosed features, functions, processes, process portions, or alternatives thereof, as well as various presently unforeseen or unanticipated alternatives, modifications, variations or improvements thereto that may be subsequently made by one of ordinary skill in the art, are encompassed by the following claims.

The invention claimed is:

1. An electrochemical method for capsaicinoid detection in a sample, the method comprising:
    contacting a screen printed electrode having a non-modified working electrode surface with the sample in the presence of an electrolyte solution, wherein said electrolyte solution includes a potassium chloride buffer; and
    determining whether a change in redox potential occurs by way of a voltammetry technique.

2. The method according to claim 1, wherein the capsaiciniod is capsaicin and dihydrocapsaicin.

3. The method according to claim 1, wherein said electrolyte solution is selected from Britton-Robinson buffer, acetate buffer, phosphate buffer, potassium chloride buffer, methanol, and acetonitrile.

4. The method according to claim 1, wherein the screen-printed electrode comprises a screen-printed carbon electrode.

5. The method according to claim 1, wherein the screen printed electrode comprises a screen-printed carbon working electrode and a screen printed silver/silver chloride reference electrode.

6. The method according to claim 1, wherein the voltammetry technique is selected from cyclic voltammetry (CV), square wave voltammetry (SWV), linear scan voltammetry (LSV), differential pulse voltammetry (DPV), and normal pulse voltammetry (NPV).

7. The method according to claim 6, wherein the voltammetry technique includes differential pulse voltammetry by way of a modulation amplitude between 0.1 to 2.0 volt/min, a step potential between approximately 0.0005 volt and approximately 0.01 volt, a modulation time of approximately 0.05 second, and a interval time of approximately 0.5 second.

\* \* \* \* \*